United States Patent
Nishizaki et al.

(10) Patent No.: US 9,987,208 B2
(45) Date of Patent: Jun. 5, 2018

(54) ELASTIN SYNTHESIS/REGENERATION PROMOTING AGENT

(71) Applicant: NISHIZAKI BIOINFORMATION RESEARCH INSTITUTE, Kobe-shi, Hyogo (JP)

(72) Inventors: Tomoyuki Nishizaki, Kobe (JP); Akito Tanaka, Toyonaka (JP)

(73) Assignee: Nishizaki Bioinformation Research Institute, Kobe (JP)

( * ) Notice: Subject to any disclaimer, the term of this patent is extended or adjusted under 35 U.S.C. 154(b) by 0 days. days.

(21) Appl. No.: 14/782,227

(22) PCT Filed: Apr. 4, 2014

(86) PCT No.: PCT/JP2014/059943
§ 371 (c)(1),
(2) Date: Oct. 2, 2015

(87) PCT Pub. No.: WO2014/163178
PCT Pub. Date: Oct. 9, 2014

(65) Prior Publication Data
US 2016/0045415 A1    Feb. 18, 2016

(30) Foreign Application Priority Data
Apr. 4, 2013   (JP) ................................ 2013-078828

(51) Int. Cl.
| | | |
|---|---|---|
| A61K 31/185 | (2006.01) | |
| C07C 61/04 | (2006.01) | |
| C07C 61/16 | (2006.01) | |
| A61K 8/36 | (2006.01) | |
| A61Q 19/08 | (2006.01) | |
| A61K 31/20 | (2006.01) | |

(52) U.S. Cl.
CPC .............. *A61K 8/361* (2013.01); *A61K 31/20* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 6,287,553 | B1 | 9/2001 | Alaluf et al. |
| 7,468,389 | B2 | 12/2008 | Nishizaki et al. |
| 9,012,500 | B2 | 4/2015 | Nishizaki et al. |
| 2005/0075393 | A1 | 4/2005 | Nishizaki et al. |
| 2009/0030055 | A1* | 1/2009 | Nelson ................ A61K 31/11 514/384 |
| 2013/0331454 | A1 | 12/2013 | Nishizaki et al. |
| 2016/0008308 | A1 | 1/2016 | Nishizaki et al. |
| 2016/0089352 | A1 | 3/2016 | Nishizaki et al. |

FOREIGN PATENT DOCUMENTS

| | | |
|---|---|---|
| JP | 2004-516277 A | 6/2004 |
| JP | 2008-143819 A | 6/2008 |
| JP | 2010-202525 A | 9/2010 |
| WO | WO 2000/037040 A1 | 6/2000 |
| WO | WO 2002/050013 A1 | 6/2002 |

OTHER PUBLICATIONS

Malinski, Journal of Alzheimer's Disease, vol. 11, No. 2, pp. 207-218, 2007.*
European Patent Office, Extended European Search Report in European Patent Application No. 14779974 (dated Sep. 12, 2016).
Kanno et al., *Biochem. J.*, 450(2): 303-309 (2013).
Kanno et al., *Cell Physiol. Biochem.*, 30(1): 75-82 (2012).
Kanno et al., *Journal of Neurochemistry*, 95(3): 695-702 (2005).
Kanno et al., *Journal of Lipid Research*, 47: 1146-1156 (2006).
Kanno et al., *Lipids*, 47(7): 687-695 (2012).
Nagata et al., *Behavioural Brain Research*, 206(1): 151-154 (2010).
Nagata et al., *Psychogeriatrics*, 5: 122-126 (2005).
Nishizaki et al., *Personalized Med. Univ.*, 3: 28-34 (2014).
Shimizu et al., *Cell Physiol. Biochem.*, 27(2): 149-158 (2011).
Tanaka et al., *Bioorganic & Medicinal Chemistry Letters*, 13(6): 1037-1040 (2003).
Yaguchi et al., *Neurochem. Res.*, 35(5): 712-717 (2010).
Yaguchi et al., *Neuropharmacology and Neurotoxicology NeuroReport*, 17(1): 105-108 (2006).
Yamamoto et al., *Neuroscience*, 130(1): 207-213 (2005).
Japanese Patent Office, International Search Report in International Patent Application No. PCT/JP2014/059943 (dated Jul. 22, 2014).
U.S. Appl. No. 10/450,816, filed Jun. 18, 2003.
U.S. Appl. No. 13/885,751, filed May 16, 2013.
U.S. Appl. No. 14/769,707, filed Aug. 21, 2015.
U.S. Appl. No. 14/891,944, filed Nov. 17, 2015.

* cited by examiner

*Primary Examiner* — Shobha Kantamneni
(74) *Attorney, Agent, or Firm* — Leydig, Voit & Mayer, Ltd.

(57) ABSTRACT

8-[2-(2-Pentyl-cyclopropylmethyl)-cyclopropyl]-octanoic acid (DCP-LA) has an action to promote synthesis and regeneration of elastin, and is useful as an agent for the prophylaxis or improvement of wrinkles, and an anti-aging drug.

8 Claims, 3 Drawing Sheets

ELASTIN SYNTHESIS/REGENERATION PROMOTING AGENT

CROSS-REFERENCE TO RELATED APPLICATIONS

This patent application is the U.S. national phase of International Patent Application No. PCT/JP2014/059943, filed Apr. 4, 2014, which claims the benefit of Japanese Patent Application No. 2013-078828, filed on Apr. 4, 2013, which are incorporated by reference in their entireties herein.

TECHNICAL FIELD

The present invention relates to a novel use of 8-[2-(2-pentyl-cyclopropylmethyl)-cyclopropyl]-octanoic acid (DCP-LA), more particularly, a use of DCP-LA as a promoter of the synthesis and/or regeneration of elastin, as an elastin fibrosis promoter, as an agent for the prophylaxis and/or improvement of wrinkle and the like.

BACKGROUND ART

8-[2-(2-Pentyl-cyclopropylmethyl)-cyclopropyl]-octanoic acid (DCP-LA), which is a linoleic acid derivative, is a compound having a long-term enhancing action on synapse transmission efficiency, which can delay metabolism in the body and can maintain stable LTP (long-term potentiation)-like enhancement of synapse transmission (patent document 1).

Some reports have also been documented as regards DCP-LA. For example, it has been reported that DCP-LA activates PKC-ε selectively and directly (non-patent document 1), DCP-LA improves cognitive dysfunction of senescence accelerated mouse (non-patent document 2), DCP-LA increases release of γ aminobutyric acid from hippocampus nerve cells (non-patent document 3), DCP-LA improves cognitive dysfunction of amyloid β peptide or scopolamine-treated rat (non-patent document 4), and DCP-LA promotes hippocampal synaptic transmission with α7 nicotinic acetylcholine receptor expressed in glutamatergic presynaptic cell as a target (non-patent document 5). Furthermore, it has been reported in recent years that DCP-LA has an action to suppress nerve cell death induced by oxidative stress (patent document 2).

On the other hand, elastin fiber is one kind of connective tissue fibers of extracellular matrix distributed in almost all systemic organs and tissues, including blood vessel, ligament, lung and skin in the body of mammals such as human and the like, fish and the like, is formed by crosslinking of stretchable α-helix structure, and is known to play an important role in the maintenance of tissue flexibility.

The skin consists of epidermis, corium, and subcutaneous tissue. Epidermis protects body from outside drying and foreign substance, subcutaneous tissue reduces impact from the outside by subcutaneous fat and the like, and corium is constituted of fibroblast and corium extracellular matrix located outside these cells and supporting the skin structure, and plays an important role in the maintenance of skin structure.

The phenomena said to be the aging of the skin such as formation of wrinkles, dullness, disappearance of texture, decrease in elasticity of the skin are partly caused by a decreased ability to produce elastin fiber and the like due to the proliferative capacity of fibroblast which became lower by aging. It is also said that exposure of skin to UV, remarkable drying of air, outside stimulation such as excessive skin wash and the like, and the like cause decomposition of elastin fiber, which in turn results in the appearance of symptoms of rough skin, skin aging and the like caused by wrinkle formation, dullness, disappearance of texture, low elasticity and the like.

Therefore, it is effective for the prevention of aging of skin such as wrinkle, flabbiness and the like to prevent decomposition of elastin fiber or promote synthesis and regeneration of elastin fiber. However, a medicament that promotes regeneration and synthesis of elastin fiber is not known at present.

DOCUMENT LIST

Patent Documents patent document 1: WO 02/50013
patent document 2: JP-A-2008-143819

Non-Patent Documents non-patent document 1: Kanno T et al., J Lipid Res., 2006, 47(6):1146-56.
non-patent document 2: Yaguchi T et al., Neuroreport, 2006, 23; 17(1):105-8.
non-patent document 3: Kanno T et al., J Neurochem., 2005, 95(3):695-702.
non-patent document 4: Nagata T et al., Psychogeriatrics, 2005, 5:122-126.
non-patent document 5: Yamamoto et al., Neuroscience 2005, 130(1):207-213.

SUMMARY OF THE INVENTION

Problems to be Solved by the Invention

The present invention aims to elucidate the pharmacological action of DCP-LA and an influence thereof on living organisms, and provide a novel use.

Means of Solving the Problems

The present inventors have surprisingly found, in the process of studying in depth the pharmacological action of DCP-LA and an influence thereof on living organisms, that DCP-LA has an action to promote synthesis and regeneration of elastin or an action to protect elastin from decomposition, in addition to the pharmacological action useful for the improvement of cognitive function and conventionally known in DCP-LA, which resulted in the completion of the present invention. Accordingly, the present invention is as described below.

[1] An elastin synthesis promoting agent comprising DCP-LA as an active ingredient.
[2] An elastin regeneration promoting agent comprising DCP-LA as an active ingredient.
[3] A fibrin-5 secretion promoting agent comprising DCP-LA as an active ingredient.
[4] An agent for the prophylaxis and/or improvement of wrinkle comprising DCP-LA as an active ingredient.
[5] An agent for the prophylaxis and/or improvement of wrinkle, comprising the promoting agent of any of the above-mentioned [1]-[3] as an active ingredient.
[6] An anti-aging drug comprising the agent of any of the above-mentioned [1]-[5].

[7] The promoting agent of any of the above-mentioned [1]-[3], which is a reagent for research.
[8] A method of promoting elastin synthesis, comprising treating a cell with DCP-LA.
[9] A method of regenerating elastin, comprising treating a cell with DCP-LA.
[10] A method of promoting fibrin-5 secretion, comprising treating a cell with DCP-LA.
[11] A method for the prophylaxis and/or improvement of wrinkle, comprising administering an effective amount of DCP-LA to a target in need thereof.

Effect of the Invention

DCP-LA has an elastin synthesis promoting action and an elastin regeneration promoting action. Furthermore, DCP-LA has an action to stimulate fibrin-5 secretion, and promote elastin fibrosis. Since the degeneration and deterioration of elastin causes wrinkles, the present invention that promotes regeneration and synthesis of elastin, and promotes elastin fibrosis is useful as an agent for the prophylaxis and/or improvement of wrinkle, a reagent for various studies, and an anti-aging drug.

DESCRIPTION OF EMBODIMENTS

Figure 1:
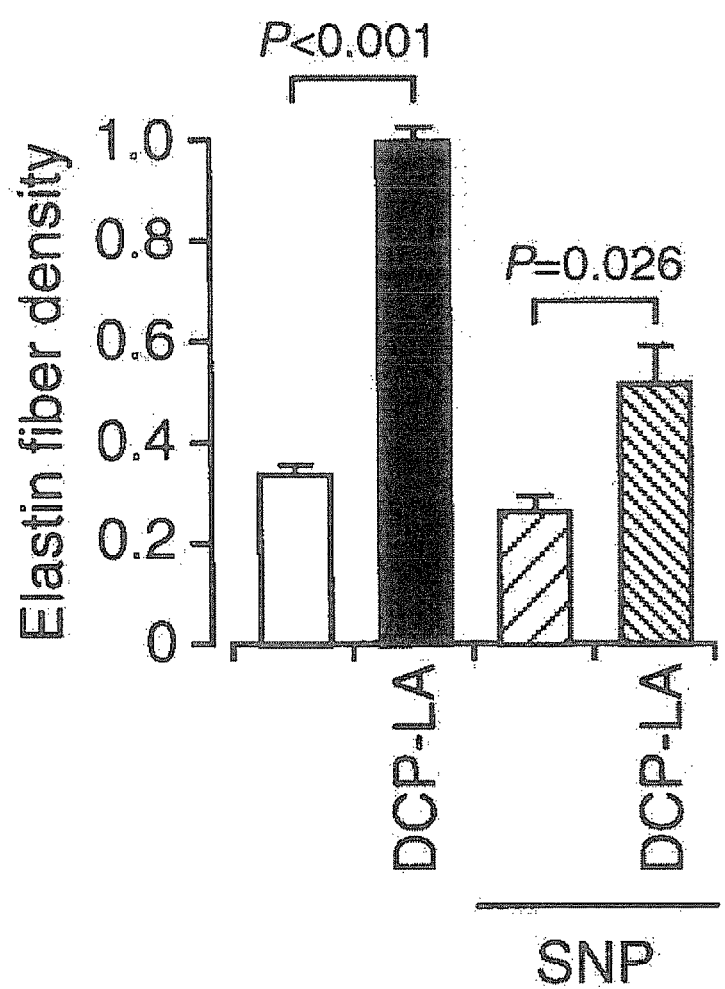
FIG. 1 is a graph showing that DCP-LA has an action to promote synthesis of elastin and an action to protect elastin from sodium nitroprusside (SNP)-inductive decomposition. Normal human skin fibroblast was treated in the presence or absence of DCP-LA (100 nM), untreated with SNP or treated with SNP (1 mM) for 12 hr. In the graph, each column shows mean (±SD) of relative density of elastin fiber relative to the DAPI density (n=4 in each experiment). P value, Dunnett's test.

The present invention is explained in detail in the following.

8-[2-(2-Pentyl-cyclopropylmethyl)-cyclopropyl]-octanoic acid (abbreviated as necessary as DCP-LA in the present specification) used in the present invention as an active ingredient has the following structural formula.

DCP-LA can be produced, for example, by the method shown in WO 02/50013. While DCP-LA has 4 optical isomers (α,α-DCP-LA, α,β-DCP-LA, β,α-DCP-LA, β,β-DCP-LA), all of such isomers and mixtures thereof are encompassed within the scope of the present invention. These isomers can be produced, for example, by the method shown in WO 2012/067111.

The DCP-LA in the present invention may also be used in the form of a salt thereof. Such salt is not particularly limited, and a salt acceptable as a medicine or food is preferable. Examples thereof include salts with inorganic base (e.g., alkali metal such as sodium, potassium and the like; alkaline earth metal such as calcium, magnesium and the like; aluminum, ammonium), organic base (e.g., trimethylamine, triethylamine, pyridine, picoline, ethanolamine, diethanolamine, triethanolamine, dicyclohexylamine, N,N-dibenzylethylenediamine), inorganic acid (e.g., hydrochloric acid, hydrobromic acid, nitric acid, sulfuric acid, phosphoric acid), organic acid (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid), basic amino acid (e.g., arginine, lysine, ornithine) or acidic amino acid (e.g., aspartic acid, glutamic acid) and the like.

When used in the present specification, the test subject can be a mammal. Examples of such mammal include primates (e.g., human, monkey, chimpanzee), rodents (e.g., mouse, rat, guinea pig), pets (e.g., dog, cat, rabbit), working animals and domestic animals (e.g., bovine, horse, swine, sheep, goat), with preference given to human.

When used in the present specification, a target cell to be treated with DCP-LA is a cell derived from the above-mentioned mammal, preferably fibroblast, keratinocyte and the like. As used herein, the "treatment" means contacting the above-mentioned cell with DCP-LA for a time necessary and sufficient. While the time varies depending on the desired effect and the kind of the cells to be used, it is generally 0.5-24 hr, preferably about 0.5-12 hr. Conveniently, it is performed by cultivation in a culture medium containing DCP-LA.

As shown in the data in the Examples, DCP-LA has an action to promote elastin synthesis and promote regeneration against nitric oxide (NO) stress induced elastin degeneration, and also has an action to protect against elastin disorder (elastin deterioration) by UV irradiation. Furthermore, as shown in the data in the Examples, DCP-LA has an action to promote secretion of fibrin-5 from fibroblast. Fibrin-5 is involved in the assembly and extension of elastin fiber, and indispensable for elastin to act as an elastic fiber in the body (i.e., fibrosis). When DCP-LA promotes secretion of fibrin-5, elastin fibrosis is promoted and the skin can have elasticity. These superior pharmacological actions suggest that DCP-LA is useful as an agent for the prophylaxis agent and/or improvement of wrinkle (hereinafter sometimes to be simply referred to as the agent of the present invention), and use as an anti-aging drug (hereinafter sometimes to be simply referred to as the medicament of the present invention) can also be expected.

An action to promote synthesis and an action to promote regeneration of elastin can be evaluated by directly measuring variation in the amount of elastin fiber by an immunohistological method and the like. In more detail, the action can be confirmed by the method described in the Examples. An action to promote fibrosis of elastin can be evaluated by measuring variation in the secretion amount (synthesis amount) of fibrin-5 by an immunohistological method and the like. In more detail, the action thereof can be confirmed by the method described in the Examples.

In one embodiment, the agent or medicament of the present invention can be formulated as a preparation preferable for oral administration. Examples of the preparation preferable for oral administration include a liquid wherein an effective amount of a substance is dissolved in a diluent such as water and saline, a capsule, granule, powder or tablet containing an effective amount of a substance as a solid or granules, a suspension wherein an effective amount of a substance is suspended in a suitable dispersion medium, an emulsion wherein a solution of an effective amount of a substance is dispersed and emulsified in a suitable dispersion medium, and the like.

In another embodiment, the agent or medicament of the present invention can be formulated as a preparation preferable for parenteral administration. Examples of the preparation preferable for parenteral administration (e.g., intravenous injection, subcutaneous injection, muscular injection, topical injection and the like) include aqueous and nonaqueous isotonic aseptic injection liquids, which may contain antioxidant, buffer, bacteriostatic, isotonicity agent and the like. In addition, examples thereof include aqueous and non-aqueous aseptic suspensions, which may contain suspending agent, solubilizer, thickener, stabilizer, preservative and the like. Unit dose or plural doses of the preparation can be filled in a container such as ampoule and vial. Moreover, the active ingredient and a pharmaceutically acceptable carrier can be freeze-dried and preserved in a form that can be dissolved or suspended in a suitable aseptic vehicle immediately before use.

In another embodiment, the agent or medicament of the present invention can be formulated as a skin external preparation. That is, DCP-LA is added to an external base, and can be used as a cosmetic, a pharmaceutical product, a quasi-drug and the like. The skin external preparation may be any as long as it is conventionally used for skin external preparations such as ointment, cream, skin milk, lotion, facial mask, bath agent and the like, and the dosage form is not particularly limited. Examples of the external base include, but are not limited to, white petrolatum, cetanol, stearyl alcohol, stearic acid, white beeswax, liquid paraffin, lauromacrogol, squalane, squalene, lanolin, isobutyl myristate, medium-chain triglyceride and the like.

From the aspect of its pharmacological action, the agent or medicament of the present invention is preferably administered to a target as an agent for parenteral administration, particularly a skin external preparation.

While the daily dose of the agent or medicament of the present invention varies depending on the age and condition of individual patients to be administered, it is 0.001-100 mg of DCP-LA per 1 kg body weight of human or animal for intravenous administration, 0.001-10 mg of the compound per 1 kg body weight of human or animal for intramuscular administration, and 0.01-100 mg of the compound per 1 kg body weight of human or animal for oral administration are generally administered for the prophylaxis and/or improvement of the above-mentioned symptom. When administered as a skin external preparation, the amount of DCP-LA in the whole preparation is not particularly limited and varies depending on the level of the expected action. It is generally 0.001-10 wt %, preferably 0.01-1 wt %, in the total amount of the agent.

The agent and/or medicament of the present invention can contain, besides DCP-LA which is the active ingredient, any additive, for example, a pharmaceutically acceptable carrier. Examples of the pharmaceutically acceptable carrier include, but are not limited to, excipients such as sucrose, starch, mannit, sorbit, lactose, glucose, cellulose, talc, calcium phosphate, calcium carbonate and the like, binders such as cellulose, methylcellulose, hydroxypropylcellulose, polypropylpyrrolidone, gelatin, gum arabic, polyethylene glycol, sucrose, starch and the like, disintegrants such as starch, carboxymethylcellulose, hydroxypropylstarch, sodium-glycol-starch, sodium hydrogen carbonate, calcium phosphate, calcium citrate and the like, lubricants such as magnesium stearate, aerosil, talc, sodium lauryl sulfate and the like, aromatic substances such as citric acid, menthol, glycyllysin-ammonium salt, glycine, orange powder and the like, preservatives such as sodium benzoate, sodium bisulfite, methylparaben, propylparaben and the like, stabilizers such as citric acid, sodium citrate, acetic acid and the like, suspending agents such as methylcellulose, polyvinylpyrrolidone, aluminum stearate and the like, dispersing agents such as surfactant and the like, diluents such as water, saline, orange juice and the like, base waxes such as cacao butter, polyethylene glycol, kerosene and the like, and the like.

DCP-LA can be provided as a food. DCP-LA as an active ingredient can be provided as an agent for the prophylaxis or improvement of wrinkles, or an anti-aging drug, or a functional food effective for the prophylaxis or improvement of wrinkles, since, as mentioned above, it has an elastin synthesis promoting action and an elastin regeneration promoting action in mammals (e.g., mouse, rat, hamster, rabbit, cat, dog, bovine, sheep, monkey, human and the like). In addition, it can be provided as a functional food expected to show an anti-aging effect.

The "food" in the present invention means all foods and drinks other than pharmaceutical products and quasi-drugs. For example, it includes, but is not limited to, food for specified health uses, food with nutrient function claims, and what is called supplements.

The agent and/or medicament of the present invention may be packed or filled individually by a unit ingestion amount or a divided amount thereof, or packed or filled comprehensively by many unit ingestion amounts or divided amounts thereof.

When the agent and/or medicament of the present invention is provided as a single preparation, the unit ingestion amount thereof or a divided amount thereof is the unit ingestion amount of DCP-LA or a divided amount thereof.

Examples of the pharmaceutical product or food wherein a unit ingestion amount or a divided amount thereof is packed or filled individually include general packages (e.g., PTP (press through packing) sheet, paper container, film (e.g., plastic film) container, glass container, plastic container) packed or filled with the unit ingestion amount or a divided amount thereof. The pharmaceutical products or foods that are individually packed or filled may be further combined and packed or filled in a single container (e.g., paper container, film (e.g., plastic film) container, glass container, plastic container). Examples of the pharmaceutical product or food wherein many unit ingestion amounts or a divided amount thereof are/is comprehensively packed or filled include those wherein many tablets or capsules are packed or filled in a single container (e.g., paper container, film (e.g., plastic film) container, glass container, plastic container) without distinction. The agent, pharmaceutical product or food of the present invention may contain a unit ingestion amount or a divided amount thereof in a number sufficient for long-term ingestion. For example, a food can contain same in a number sufficient for ingestion for not less than 3 days, preferably not less than 7 days, 10 days, 14 days or 21 days, or 1 month, 2 months, or not less than 3 months.

The agent and/or medicament of the present invention may contain, in addition to the essential active ingredient DCP-LA, one or more kinds of other components useful for the prophylaxis•improvement of wrinkles or anti-aging.

Examples of such component include vitamins, amino acid, moisturizer, UV absorber, astringent, antioxidant, anti-inflammatory agent, sterilizer, antiseptic and the like.

Examples of vitamins include retinol, retinal (vitamin A1), dehydroretinal (vitamin A2), carotene, lycopene (pro-vitamin A) for vitamin A group, thiamine hydrochloride, thiamine sulfate (vitamin B1), riboflavin (vitamin B2), pyridoxine (vitamin B6), cyanocobalamin (vitamin B12), folic acids, nicotinic acids, pantothenic acids, biotins, choline, inositols for vitamin B group, ascorbic acid and a derivative thereof for vitamin C group, ergocalciferol (vitamin D2), cholecalciferol (vitamin D3) and dihydrotachysterol for vitamin D group, tocopherol and a derivative thereof, and ubiquinones for vitamin E group, and phytonadione (vitamin K1), menaquinone (vitamin K2), menadione (vitamin K3), menadiol (vitamin K4) and the like for vitamin K group.

Examples of amino acid include valine, leucine, isoleucine, threonine, methionine, phenylalanine, tryptophan, lysine, glycine, alanine, asparagine, glutamine, serine, cysteine, cystine, tyrosine, proline, hydroxyproline, aspartic acid, glutamic acid, hydroxylysine, arginine, ornithine, histidine and the like, amino acid derivatives such as sulfate, phosphate, nitrate, citrate, or pyrrolidonecarboxylic acid thereof, and the like.

Examples of the moisturizer include hyaluronic acid, polyglutamic acid, serine, glycine, threonine, alanine, collagen, hydrolyzed collagen, hydronectin, fibronectin, keratin, elastin, royal jelly, chondroitin sulfate heparin, glycerolphospholipid, glycerolglycolipid, sphingophospholipid, sphingoglycolipid, linoleic acid or esters thereof, eicosapentaenoic acid or esters thereof, pectin, bifidobacteria fermentation product, lactic acid fermentation product, yeast extract, reishi mycelium culture or extract thereof, wheat germ oil, avocado oil, rice germ oil, jojoba oil, soybean phospholipid, γ-oryzanol, Althaea officinalis extract, coix seed extract, Rehmanniae radix extract, Jujube extract, seaweed extract, Aloe arborescens extract, burdock extract, rosemary extract, arnica extract, wheat bran and the like.

Examples of the UV absorber include p-aminobenzoic acid derivative, salicylic acid derivative, anthranilic acid derivative, coumarin derivative, amino acid compound, benzotriazole derivative, tetrazole derivative, imidazoline derivative, pyrimidine derivative, dioxane derivative, camphor derivative, furan derivative, pyrrone derivative, nucleic acid derivative, allantoin derivative, nicotinic acid derivative, vitamin B6 derivative, oxybenzone, benzophenone, guaiazulene, shikonin, baicalin, baicalein, berberine and the like.

Examples of the astringent include lactic acid, tartaric acid, succinic acid, citric acid, allantoin, zinc chloride, zinc sulfate, zinc oxide, calamine, zinc p-phenolsulfonate, aluminum potassium sulfate, resorcin, ferric chloride, tannic acid and the like.

Examples of the antioxidant include ascorbic acid and a salt thereof, stearic acid ester, tocopherol and ester derivative thereof, nordihydroguaceretic acid, butylhydroxytoluene (BHT), butylhydroxyanisole (BHA), para hydroxyl anisole, propyl gallate, sesamol, sesamolin, gossypol and the like.

Examples of the anti-inflammatory agent include icthhammol, indomethacin, kaolin, salicylic acid, sodium salicylate, methyl salicylate, acetylsalicylic acid, diphenhydramine hydrochloride, d or dl-camphor, hydrocortisone, guaiazulene, chamazulene, chlorpheniramine maleate, glycyrrhizic acid and a salt thereof, glycyrrhetinic acid and a salt thereof and the like.

Examples of the sterilizer and antiseptic include acrinol, sulfur, benzalkonium chloride, benzethonium chloride, methylrosanilinium chloride, cresol, calcium gluconate, chlorhexidine gluconate, mercurochrome, lactoferrin or hydrolysate and the like.

The contents disclosed in any publication cited in the present specification, including patents and patent applications, are hereby incorporated in their entireties by reference, to the extent that they have been disclosed herein.

While the present invention is explained in further detail in the following by referring to Examples, it is not limited by the following Examples and the like.

EXAMPLES

Example 1: Synthesis and Regeneration Promoting Action on Elastin Fiber and Protecting Action Against Elastin Disorder (Materials and Methods)
1. Cell Culture Normal human fibroblast was purchased from Lonza (Verviers, Belgium). The cells were cultured in FGM™-2 BulletKit™ (Lonza) at 5% $CO_2$ and 95% air under wet atmosphere at 37° C.

2. Animal

Male HR-1 hairless mice (7- to 8-week-old) were purchased from Japan SLC. Inc. (Shizuoka, Japan). The mice were reared in a chamber at controlled temperature in a cycle of 12 hr light conditions/12 hr dark conditions.

3. Ultraviolet (UV) Irradiation

The mice were transferred to a special cage provided with a UV light on the roof and reared therein. UV light was continuously irradiated on the back skin at a distance of 12 cm for the whole 2 weeks.

4. Preparation of DCP-LA

During UV irradiation, DCP-LA (1 mg/ml) diluted with polyethylene glycol (PEG) was applied to the skin of the back of the mouse once per day.

5. Immunocytological Measurement

In the presence or absence of DCP-LA (100 nM), normal human skin fibroblasts were treated with sodium nitroprusside (SNP) (1 mM). Then, the cells were fixed with methanol at −20° C. for 30 min, and blocked with 2% (w/v) bovine serum albumin-containing phosphate buffered saline (PBS) at room temperature. The cells were reacted with an anti-elastin antibody (1:100) (Millipore, Temecula, Calif., USA) at 4° C. overnight, and then reacted with an Alexa488-conjugated goat anti-mouse IgG antibody (Molecular Probes, Eugene, Oreg., USA) at room temperature for 1 hr. After staining with 4',6-diamidino-2-phenylindole (DAPI), the fluorescence-labeled cells were visualized with a confocal scanning laser microscope (Axiovert/LSM510; Carl Zeiss, Oberkochen, Germany). The fluorescence signal intensity of the elastin fiber was analyzed using ImageJ (Bethesda, Md., USA). The intensity of the elastin fiber was standardized by the intensity of DAPI.

6. Immunohistological Measurement

The mice were sacrificed, a skin block was mounted on OTC (optimal cutting temperature compound), and cut out in about 10 μm thickness by a cryostat. A section was blocked with 5% (v/v) goat serum in PBS-Triton X-100 for 1 hr. Then, the section was incubated with an anti-elastin mouse monoclonal antibody (1:2000) (Millipore), which is the primary antibody, at 4° C. overnight, and then incubated with a goat anti-mouse IgG antibody (1:500) (Invitrogen, Carlsbad, Calif., USA) which is the secondary antibody, for 1 hr at room temperature. After staining with DAPI, the section was visualized with a confocal scanning laser microscope (Axiovert/LSM510; Carl Zeiss). The fluorescence signal intensity of the elastin fiber was quantified by NIH image. The intensity of the elastin fiber was standardized by the intensity of DAPI.

7. Western Blotting

The cultured normal human skin fibroblast was treated with DCP-LA (100 nM) for 0-24 hr, and the culture medium was recovered. After precipitation with 5% (w/v) trichloroacetic acid, protein was separated by sodium dodecyl sulfate-polyacrylamide electrophoresis (SDS-PAGE) using TGX gel (BioRad, Hercules, Calif., USA) and transferred on a polyvinylidene difluoride membrane. The blotting membrane was blocked with TBS-T [150 mM NaCl, 0.1% (v/v) Tween20 and 20 mM Tris, pH 7.5] containing 5% (w/v) BSA, and reacted with anti-fibrin-5 antibody (Sigma, St Louis, Mo., USA). After washing, the membrane was reacted with horseradish peroxidase-conjugated goat anti-rabbit IgG antibody. The immune reactivity was detected by ECL kit (GE Healthcare, Piscataway, N.J., USA), and visualized using a chemiluminescence detection system (GE Healthcare). The protein concentration of each sample was measured using a BCA protein assay kit (Thermo Fisher Scientific, Waltham, Mass., USA).

8. Statistical Analysis

Statistical analysis was performed using the Dunnett's test.

(Results)

Figure 2:
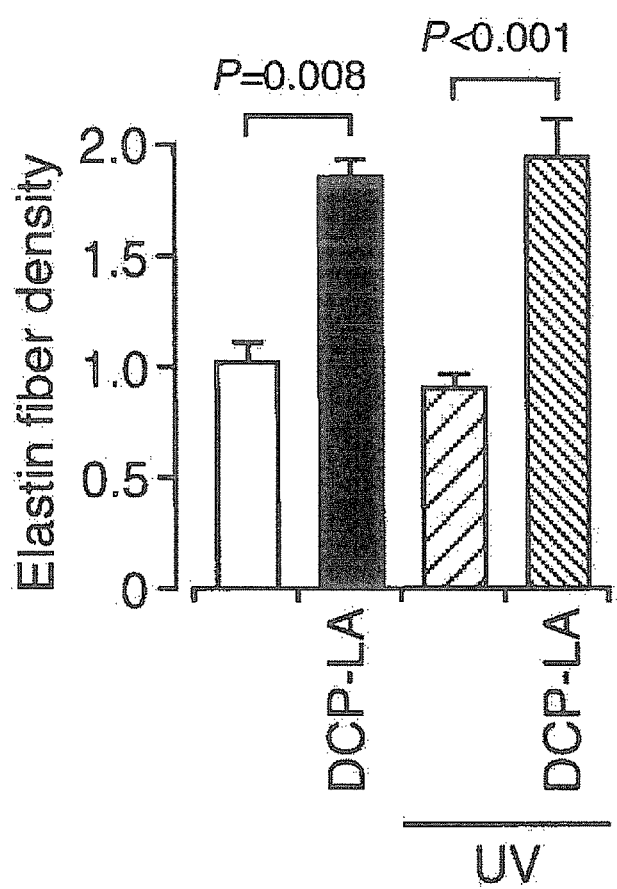
FIG. 2 is a graph showing that DCP-LA has an action to protect elastin fiber from elastin loss by UV irradiation. DCP-LA (1 mg/ml) was applied or not applied to the back skin of a mouse, and UV was not or was irradiated for 2 weeks. In the graph, each column shows mean (±SEM) of relative density of elastin fiber relative to the DAPI density (n=4 in each experiment). P value, Dunnett's test.

The results of experiments using normal human skin fibroblast are shown in FIG. 1, and the results of experiments using an animal (mouse) are shown in FIG. 2.

As shown in FIG. 1, DCP-LA is suggested to have an action to promote elastin synthesis and promote regeneration against elastin degeneration induced by NO stress. In other words, DCP-LA is suggested to act for the prophylaxis of wrinkles and improvement of wrinkles.

The largest factor of wrinkle is said to be exposure to UV. As shown in FIG. 2, DCP-LA has a protecting action against elastin disorder (elastin deterioration) caused by UV irradiation. This shows that DCP-LA acts to prevent wrinkles and improve wrinkles of in vivo wrinkle models.

Figure 3:
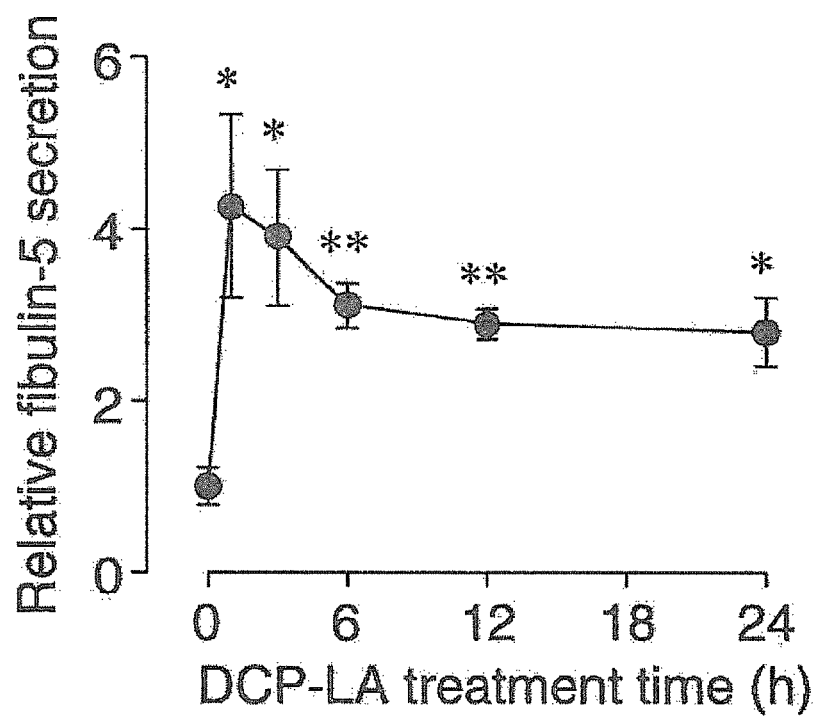
FIG. 3 is a graph showing that DCP-LA has an action to stimulate secretion of fibrin-5 from normal human skin fibroblast. The amount of fibrin-5 secreted from normal human fibroblast in a culture medium was measured at a given time before and after DCP-LA (100 nM) treatment. The measurement was performed by Western blot using anti-fibrin-5 antibody. In the graph, each point shows mean (±SEM) of relative value relative to the developed color intensity of fibrin-5 at the time point (0 h) to be the standard (n=4 in each experiment). *P<0.05, **P<0.01, developed color intensity of fibrin-5 at the time point to be the standard, Dunnett's test.

Also, as shown in FIG. 3, treatment with DCP-LA increased the secretion amount of fibrin-5. Since the secretion amount of fibrin-5 necessary for fibrosis of elastin increases, fibrosis of elastin is promoted, which in turn can impart elasticity to the skin.

INDUSTRIAL APPLICABILITY

DCP-LA has an action to promote elastin synthesis and promote regeneration against elastin degeneration induced by nitric oxide (NO) stress, and also has a protecting action against elastin disorder (elastin deterioration) caused by UV irradiation. Therefore, it is useful for the prophylaxis and/or improvement of wrinkles, and use as an anti-aging drug is expected.

This application is based on patent application No. 2013-078828 filed in Japan on Apr. 4, 2013, the contents of which are encompassed in full herein.

The invention claimed is:

1. A method of promoting elastin synthesis or regeneration of skin, comprising administering an effective amount of 8-[2-(2-pentyl-cyclopropylmethyl)-cyclopropyl]-octanoic acid (DCP-LA) as a dermatological external preparation comprising 0.001-10 wt. % DCP-LA to fibroblasts, keratinocytes, or both fibroblasts and keratinocytes of a subject without cognitive dysfunction that has elastin loss caused by nitric oxide (NO) stress and/or ultraviolet (UV) irradiation, thereby promoting elastin synthesis or regeneration of skin in the subject.

2. The method according to claim 1, wherein fibrin-5 secretion is promoted.

3. The method according to claim 1, which causes prophylaxis and/or improvement of a wrinkle of skin.

4. The method of claim 3, wherein the external preparation is selected from the group consisting of an ointment, cream, skin milk, lotion, facial mask, and bath agent.

5. The method of claim 1, wherein the subject is a human.
6. The method of claim 2, wherein the subject is a human.
7. The method of claim 3, wherein the subject is a human.
8. The method of claim 4, wherein the subject is a human.

* * * * *

UNITED STATES PATENT AND TRADEMARK OFFICE
CERTIFICATE OF CORRECTION

PATENT NO. : 9,987,208 B2
APPLICATION NO. : 14/782227
DATED : June 5, 2018
INVENTOR(S) : Nishizaki et al.

It is certified that error appears in the above-identified patent and that said Letters Patent is hereby corrected as shown below:

In the Claims

Claim 1, Column 10, Line 29, insert --in need thereof-- after "subject"

Signed and Sealed this
Second Day of October, 2018

Andrei Iancu
*Director of the United States Patent and Trademark Office*